Oct. 4, 1932. L. R. TAFT Plant Pat. 29

CHERRY

Filed March 16, 1932

Inventor:
L. R. TAFT
By Robb & Robb
Attorneys

Patented Oct. 4, 1932 Plant Pat. 29

UNITED STATES PATENT OFFICE

LEVI R. TAFT, OF EAST JORDAN, MICHIGAN, ASSIGNOR TO STARK BRO'S NURSERIES & ORCHARDS COMPANY, OF LOUISIANA, MISSOURI

CHERRY

Application filed March 16, 1932. Serial No. 599,298.

The present invention or discovery relates to a variety of cherry tree, a bud sport of the variety known as Montmorency cherry. The Montmorency is one of the best known "so-called" sour cherries, the cherry not being in reality a sour cherry, for when ripe it is sweet and luscious. It is particularly excellent for canning and preserving.

Grown under comparable conditions in the same orchard, the new variety herein described is, with one exception, identical with the Montmorency. This refers both to the original tree and to second general trees. The exception resides in the seasoning or ripening, for when grown under comparable conditions, the fruit of this new variety ripens from ten days to two weeks later than the regular or true Montmorency. This later ripening habit I have found from propagation remains a constant factor and is a very valuable characteristic in that it practically doubles the picking and canning season for Montmorency cherries. One of the difficulties of canneries lies in the large investment necessary in equipment which can be used only for a short period of time during the year and of course when the canning period can be measurably increased gluts are relieved, labor is facilitated and from the grower's standpoint, the problem of picking a large crop in a very short time is simplified.

As above indicated the tree in size, shape and growth is identical with the best type of Montmorency. This holds true as to branches, foliage and fruit. The time of blooming is slightly different and in its favor, inasmuch as it escapes the severe freezes to which the early cherries are subjected.

The drawing hereto annexed illustrates more or less graphically the substantial difference between the stages of ripening of this new variety in comparison with certain other cherries, the full ripe or picking stage of the early cherry being taken as the basis.

In the drawings:—

Figure 3:
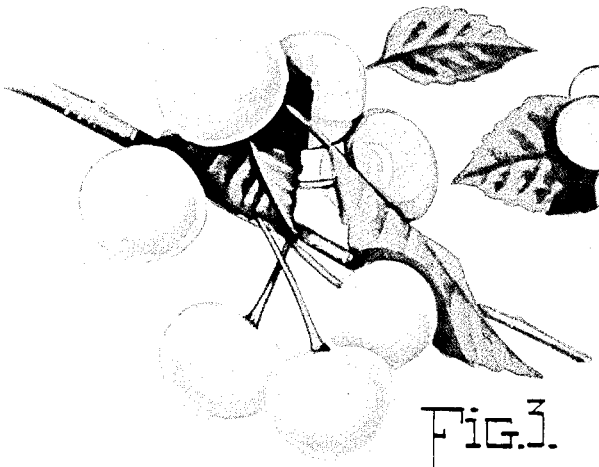
Fig. 3 represents the comparative ripening condition at this time of the true Montmorency.
Figure 4:
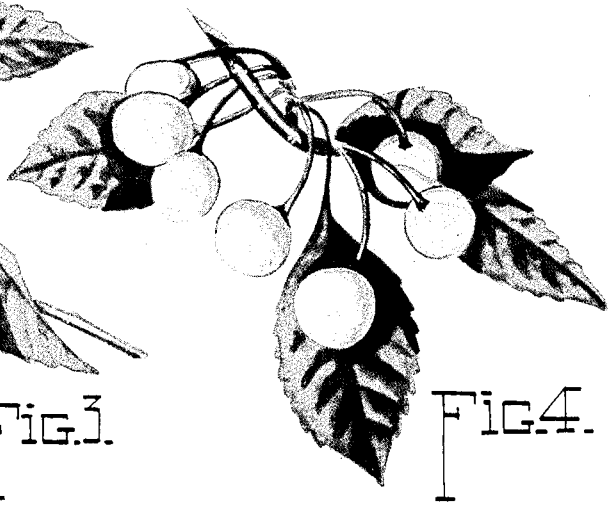
Fig. 4 shows the ripening condition of this new variety herein set forth in relation to said true Montmorency.
Figure 1:
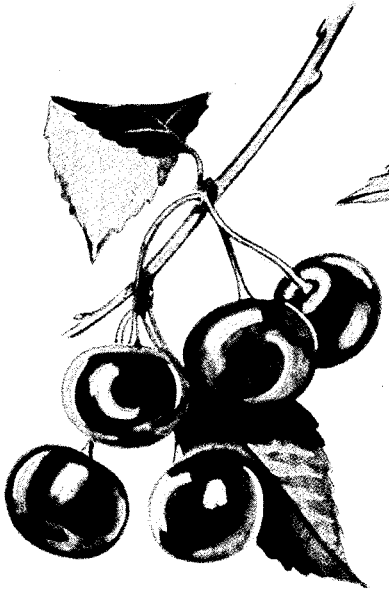
Fig. 1 represents the full ripe stage of the well known early cherry called "Early Richmond"
Figure 2:
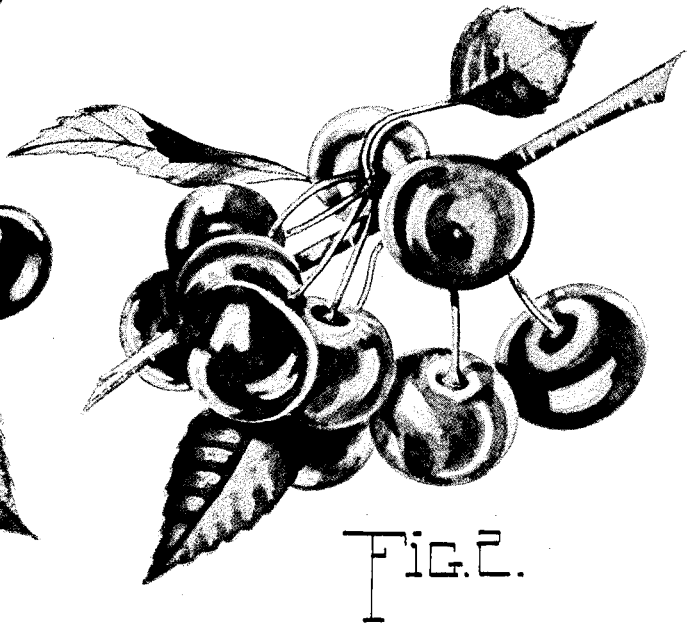
Fig. 2 represents the same stage of what I may term an early Montmorency which forms the subject matter of a separate copending application Serial Number 599,299.

The following is a more specific description of this new variety:

*Leaves.*—Mature leaves on new growth medium to large. Form long—oval; size medium: 3½ to 4 inches long, 1½ to 1¾ inches wide. Texture rather heavy. Upper surface smooth, slightly glossy, dark green. Lower surface smooth, much lighter in color with prominent pale green midrib and distinctly traced veins. Base broadly rounded; margin double crenate, glandular tipped. Apex pointed, almost acuminate. Petiole stout, tinged with purplish-red; ½ to ¾ inch long. Stipules very prominent on vigorous new growth; acuminate and serrate. Glands two or more, sometimes poorly developed. When normal are large, round and yellowish brown. Twigs of new growth rather slender, green with brownish tinge.

*Fruit.*—Maturity very late, ten days after Montmorency. Size medium: $\frac{11}{16}$ inch in axial diameter, $\frac{13}{16}$ inch longest transverse diameter, $\frac{12}{16}$ inch shortest transverse diameter. Form roundish-oblate with broad base and slightly flattened apex. Stem slender, medium to rather long, 1⅜ to 1½ inches. Cavity fairly wide and deep; suture very slightly indented or merely a line. Color bright scarlet to deep scarlet when fully mature. Dots minute, submerged, yellowish. Surface smooth, glossy. Skin thin; tough. Flesh rather firm, very juicy, slightly fibrous; translucent. Color modified by skin and pit coloring and prominent whitish veins. Juice abundant, almost colorless. Flavor slightly acid, somewhat aromatic. Quality, very good.

*Seed.*—Stone small; free from flesh, smooth, pale buff color; rounded. Size ⅜ inch long, ⅜ inch wide, ¼ inch thick. Ventral suture a line; dorsal suture prominent, ridged. Base broad; apex almost round.

I claim:

The cherry tree herein described, characterized by the lateness of ripening period of its fruit, as shown.

In testimony whereof, I affix my signature.

LEVI R. TAFT.